US00PP37788P3

(12) United States Plant Patent
de Vos

(10) Patent No.: US PP37,788 P3
(45) Date of Patent: Oct. 20, 2026

(54) ***HYDRANGEA* PLANT NAMED 'HYLV18539'**

(50) Latin Name: *Hydrangea paniculata*
Varietal Denomination: HYLV18539

(71) Applicant: KWEKERIJ LENDERT de VOS B.V., Reeuwijk (NL)

(72) Inventor: Lendert de Vos, Reeuwijk (NL)

(73) Assignee: KWEKERIJ LENDERT de VOS B.V., Reeuwijk (NL)

( * ) Notice: Subject to any disclaimer, the term of this patent is extended or adjusted under 35 U.S.C. 154(b) by 0 days.

(21) Appl. No.: 19/339,077

(22) Filed: Sep. 24, 2025

(65) Prior Publication Data

US 2026/0206663 P1 Jul. 16, 2026

Related U.S. Application Data

(60) Provisional application No. 63/746,242, filed on Jan. 16, 2025.

(51) Int. Cl.
*A01H 5/02* (2018.01)
*A01H 6/48* (2018.01)

(52) U.S. Cl.
USPC ..... Plt./250
CPC ..... *A01H 6/48* (2018.05); *A01H 5/02* (2013.01)

(58) Field of Classification Search
USPC ..... Plt./250
CPC ..... A01H 5/02; A01H 5/00; A01H 6/48
See application file for complete search history.

(56) References Cited

PUBLICATIONS

Facebook Võiste Puukool 2024 retrieved on Dec. 17, 2025 at https://www.facebook.com/100057348134932/photos/970427484878847/, one page. (Year: 2024).*
Gardenlights *Hydrangea* retrieved on Dec. 17, 2025 at https://hydrangeagardenlights.nl/Gardenlights-Hydrangea-Collection/, pp. 2-16. (Year: 2025).*
Google translation retrieved on Dec. 17, 2025 at https://www.google.com/search?q=translation&safe=active&sca_esv=27bf74d1c97a8942&rlz=1C1GCEA_enUS1032US1033&ei=. . . one page. (Year: 2025).*
Lendert de Vos Garden Lights retrieved on Dec. 17, 2025 at https://lendertdevos.nl/gardenlights-collection/, 11 pp. (Year: 2025).*

* cited by examiner

*Primary Examiner* — June Hwu
(74) *Attorney, Agent, or Firm* — C. Anne Whealy

(57) ABSTRACT

A new and distinct cultivar of *Hydrangea* plant named 'HYLV18539', characterized by its compact, upright to broadly spreading plant habit; moderately vigorous growth habit; freely branching habit; strong and sturdy stems; freely flowering habit; panicles with yellowish green-colored sterile flowers; and good postproduction longevity.

2 Drawing Sheets

Figure 1:
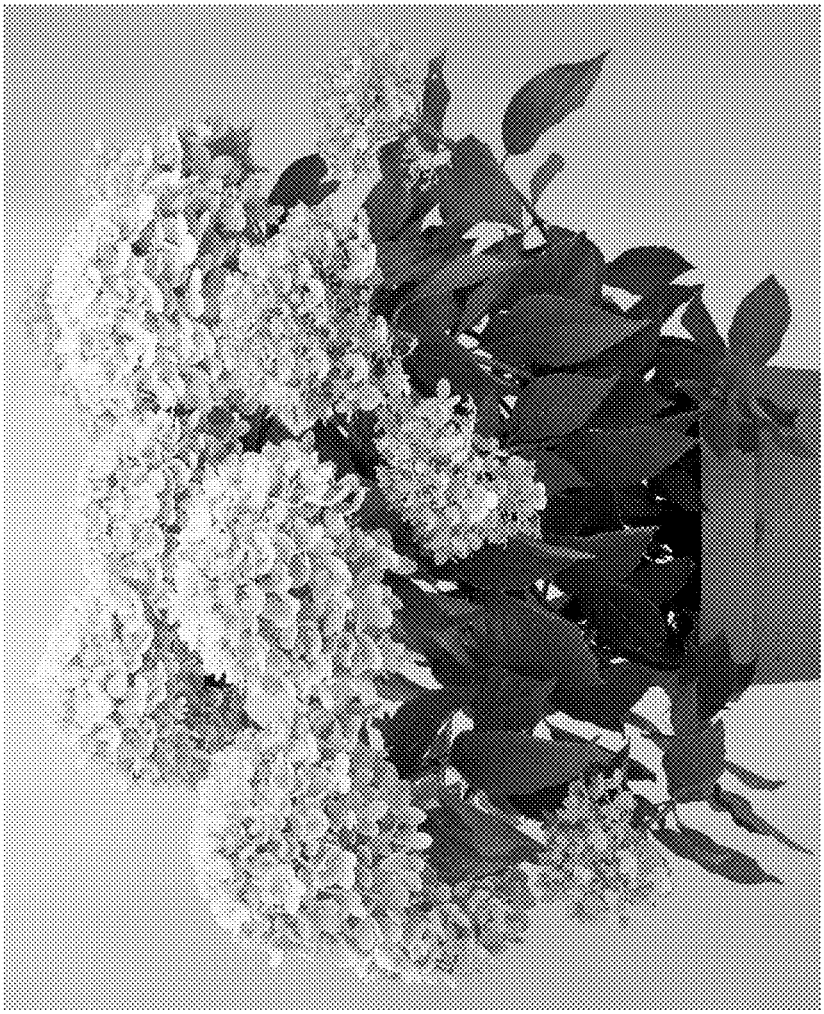

Botanical designation: *Hydrangea paniculata.*
Cultivar denomination: 'HYLV18539'.

CROSS-REFERENCED TO CLOSELY-RELATED APPLICATIONS

A European Community Plant Breeder's Rights application for this plant was filed by the Applicant/Assignee of the instant application, Kwekerij Lendert de Vos of Reeuwijk, The Netherlands on Sep. 24, 2024, application number 2024/2231, and published on Dec. 15, 2024. Foreign priority is not claimed to this European Plant Breeder's Rights application.

A United Kingdom Plant Breeder's Rights application for this plant was filed by the Applicant/Assignee of the instant application, Kwekerij Lendert de Vos of Reeuwijk, The Netherlands on Sep. 30, 2024, application number 23/888, and published on Oct. 1, 2024. Foreign priority is not claimed to this United Kingdom Plant Breeder's Rights application.

A Provisional U.S. Patent application for this plant was filed by the Inventor of the instant application, Mr. Lendert de Vos of Reeuwijk, The Netherlands on Jan. 16, 2025, application Ser. No. 63/746,242. Priority is claimed to this Provisional U.S. Patent application.

BACKGROUND OF THE INVENTION

The present invention relates to a new and distinct cultivar of *Hydrangea* plant, botanically known as *Hydrangea paniculata*, commercially referred to as a Paniculated *Hydrangea* and hereinafter referred to by the name 'HYLV18539'.

The new *Hydrangea* plant is a product of a planned breeding program conducted by the Inventor in Reeuwijk, The Netherlands. The objective of the breeding program is to create new compact and strong *Hydrangea* plants with large inflorescences and good postproduction longevity.

The new *Hydrangea* plant originated from an open-pollination in August, 2017 of *Hydrangea paniculata* 'HYLV02', disclosed in U.S. Plant Pat. No. 31,237, as the female, or seed, parent with an unknown selection of *Hydrangea paniculata* as the male, or pollen, parent. The new *Hydrangea* plant was discovered and selected as a single flowering plant from within the progeny of the stated open-pollination in a controlled greenhouse environment in Reeuwijk, The Netherlands in August, 2018.

Asexual reproduction of the new *Hydrangea* plant by terminal vegetative cuttings since August, 2018 in a controlled greenhouse environment in Reeuwijk, The Netherlands has shown that the unique features of this new *Hydrangea* plant are stable and reproduced true to type in successive generations of asexual reproduction.

SUMMARY OF THE NEW PLANT

Plants of the new *Hydrangea* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'HYLV18539'. These characteristics in combination distinguish 'HYLV18539' as a new and distinct *Hydrangea* plant:

1. Compact, upright to broadly spreading plant habit.
2. Moderately vigorous growth habit.
3. Freely branching habit.
4. Strong and sturdy stems.
5. Freely flowering habit.
6. Panicles with yellowish green-colored sterile flowers.
7. Good postproduction longevity.

Plants of the new *Hydrangea* can be compared to plants of the female parent, 'HYLV02'. Plants of the new *Hydrangea* differ primarily from plants of 'HYLV02' in sterile flower sepal color as sterile flower sepals of plants of the new *Hydrangea* are yellowish green in color whereas sterile flower sepals of plants of 'HLYV02' are light green to white in color. In addition, with subsequent development, sterile flower sepals of plants of the new *Hydrangea* become darker yellowish green in color whereas sterile flower sepals of plants of 'HYLV02' become red purple in color.

Plants of the new *Hydrangea* can be compared to plants of *Hydrangea paniculata* 'Limelight', disclosed in U.S. Plant Pat. No. 12,874. In side-by-side comparisons, plants of the new *Hydrangea* differ primarily from plants of 'Limelight' in the following characteristics:

1. Plants of the new *Hydrangea* are more compact and have shorter lateral branches than plants of 'Limelight'.
2. Inflorescences of plants of the new *Hydrangea* are broadly conical to roughly flattened globular in shape whereas inflorescences of plants of 'Limelight' are pyramidal in shape.
3. Sterile flower sepals of plants of the new *Hydrangea* are darker yellowish green in color than sterile flower sepals of plants of 'Limelight'.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet (FIG. 1) is a side perspective view of a typical flowering plant of 'HYLV18539' grown in a container.

Figure 2:
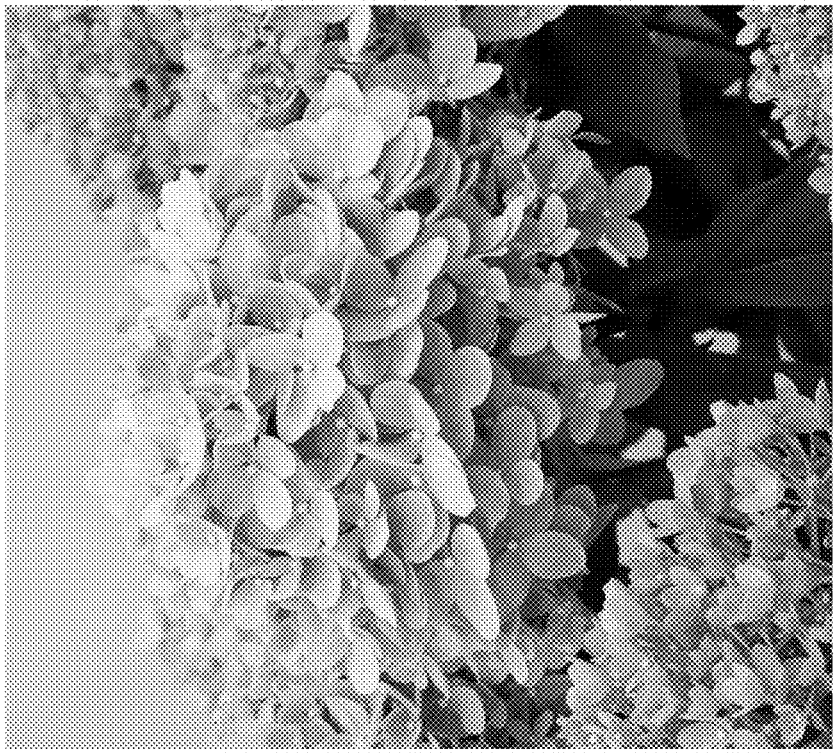

The photograph on the left of the second sheet (FIG. 2) is a close-up view of typical inflorescences of 'HYLV18539'.

Figure 3:
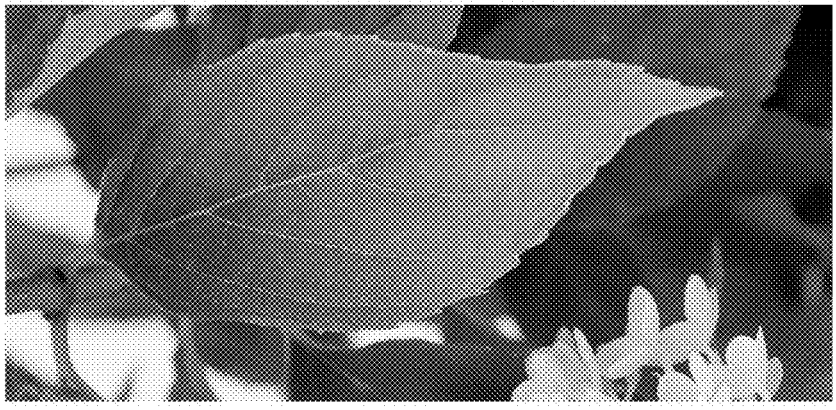

The photograph on the right of the second sheet (FIG. 3) is a close-up view of a typical leaf of 'HYLV18539'.

DETAILED BOTANICAL DESCRIPTION

Plants used in the aforementioned photographs and in the following description were grown during the summer in 23-cm containers in an outdoor nursery in Reeuwijk, The Netherlands and under cultural practices typical of commercial *Hydrangea* production. During the production of the plants, day temperatures ranged from 18° C. to 32° C. and night temperatures ranged from 12° C. to 20° C. Plants of the new *Hydrangea* were two years old when the photographs and description were taken. In the following description, color references are made to The Royal Horticultural Society Colour Chart, Sixth Edition, except where general terms of ordinary dictionary significance are used. Plants of the new *Hydrangea* plant is not typically treated with aluminum sulfate to "blue" the flower color.

Botanical description: *Hydrangea paniculata* 'HYLV18539'.

Parentage:

*Female, or seed, patent.*—*Hydrangea paniculata* 'HYLV02', disclosed in U.S. Plant Pat. No. 31,237.

*Male, or pollen, patent.*—Unknown selection of *Hydrangea paniculata*, not patented.

Propagation:

*Type cutting.*—By vegetative terminal cuttings.

*Time to initiate roots, summer.*—About 16 days at temperatures ranging from 20° C. to 30° C.

*Time to produce a rooted young plant, summer.*—About four months at temperatures ranging from 20° C. to 30° C.

*Root description.*—Medium in thickness; fibrous; typically light brown in color, actual color of the roots is dependent on substrate composition, water quality, fertilizer type and formulation, substrate temperature and physiological age of roots.

*Rooting habit.*—Freely branching; dense.

Plant description:

*Plant and growth habit.*—Compact; upright to broadly outwardly spreading and mounding plant habit; overall shape, broadly obovate; strong and sturdy stems; moderately vigorous growth habit and moderate growth rate; about one year from propagation are required to produce small finished plants.

*Plant height.*—About 45.8 cm.

*Plant diameter or area of spread.*—About 59.2 cm.

Lateral branch description:

*Branching habit.*—Freely branching habit with about 17 lateral branches developing per plant; pinching is not required, but will enhance lateral branch development.

*Length.*—About 25.3 cm.

*Diameter.*—About 5 mm.

*Internode length.*—About 4.8 cm.

*Strength.*—Strong, sturdy.

*Aspect.*—Erect to about 60° from vertical.

*Texture.*—Sparsely pubescent; becoming woody with subsequent development.

*Color, developing.*—Close to 144B.

*Color, fully developed.*—Close to 148B, N148A, 194A and 195A; older bark, close to 197A, 199B and N200B.

*Lenticels*.—Density: Sparse. Length: About 1.5 mm. Diameter: About 0.75 mm. Color: Close to 164B and 164C.

Leaf description:

*Arrangement*.—Opposite or in whorls of three, simple.

*Length*.—About 10.2 cm.

*Width*.—About 5.2 cm.

*Shape*.—Elliptic to elliptic-ovate; slightly carinate.

*Apex*.—Apiculate.

*Base*.—Acute.

*Margin*.—Serrate.

*Texture and luster, upper surface*.—Sparsely pubescent; slightly glossy.

*Texture and luster, lower surface*.—Mostly glabrous; venation, sparsely pubescent; slightly glossy.

*Venation pattern*.—Pinnate.

*Color*.—Developing leaves, upper surface: Close to 143A. Developing leaves, lower surface: Close to 146B. Fully developed leaves, upper surface: Close to 137B; venation, close to 146A. Fully developed leaves, lower surface: Close to 147B; venation, close to 146D.

*Petioles*.—Length: About 1.2 cm. Diameter: About 2.5 mm. Texture and luster, upper surface: Smooth, glabrous; slightly glossy. Texture and luster, lower surface: Sparsely pubescent; slightly glossy. Color, upper surface: Close to 146B. Color, lower surface: Close to 144A and 144B.

Flower description:

*Flower type and habit*.—Showy rotate sterile flowers and small, inconspicuous rotate fertile flowers arranged on terminal panicles; panicles broadly conical to roughly flattened globular in shape; sterile flowers face upright, outwardly to slightly drooping and fertile flowers face mostly upright.

*Fragrance*.—Faintly fragrant; sweet and pleasant.

*Natural flowering season*.—Plants flower continuously for about three months; in garden in The Netherlands, plants flower from midsummer into the late summer.

*Flower longevity*.—Good postproduction longevity; sterile flowers maintain good substance for about six weeks on the plant, sterile flowers persistent; fertile flowers last for about five days on the plant, fertile flowers not persistent.

*Quantity of flowers*.—Freely flowering habit; about 450 sterile flowers per panicle and about 200 fertile flowers per panicle.

*Panicle height*.—About 13.1 cm.

*Panicle diameter*.—About 15.1 cm.

*Panicle peduncles*.—Length: About 10 cm. Diameter: About 3 mm. Strength: Moderately strong. Aspect: Primary peduncles, erect; lateral peduncles, about 45° from primary peduncle axis. Texture and luster: Moderately pubescent; matte. Color: Close to a blend of 147D and 193A.

*Sterile flower buds*.—Length: About 7 mm. Diameter: About 8 mm. Shape: Cup-shaped. Color: Close to 145C.

*Fertile flower buds*.—Length: About 4 mm. Diameter: About 3 mm. Shape: Obovate. Color: Immature corolla, close to 157C and 157D, and immature calyx, close to 145B and 145C.

*Sterile flower diameter*.—About 3.3 cm.

*Sterile flower depth (height)*.—About 7 mm.

*Fertile flower diameter*.—About 8.5 mm.

*Fertile flower depth (height)*.—About 5 mm.

*Petals, sterile flowers*.—Quantity and arrangement: Typically, four; occasionally five in a single whorl. Length: About 3 mm. Width: About 1.5 mm. Shape: Ovate; strongly concave. Apex: Acute. Base: Cuneate. Margin: Entire. Texture and luster, upper and lower surfaces: Smooth, glabrous; slightly glossy. Color: When opening, upper surface: Close to 145A. When opening, lower surface: Close to 145D. Fully opened, upper and lower surfaces: Close to 145D; color does not change with subsequent development.

*Petals, fertile flowers*.—Quantity and arrangement: Five in a single whorl. Length: About 3 mm. Width: About 2 mm. Shape: Broadly ovate; slightly concave. Apex: Acute. Base: Cuneate. Margin: Entire. Texture and luster, upper surface: Smooth, glabrous; slightly glossy. Texture and luster, lower surface: Smooth, glabrous; matte. Color: When opening and fully opened, upper surface: Close to 157C; color does not change with subsequent development. When opening and fully opened, lower surface: Close to 145D; color does not change with subsequent development.

*Sepals, sterile flowers*.—Quantity and arrangement: Typically, four; occasionally five in a single whorl. Length: About 2 cm. Width: About 1.5 cm. Shape: Elliptic to elliptic-obovate and obovate; slightly concave. Apex: Obtuse to shallowly retuse. Base: Cuneate. Margin: Entire. Texture and luster, upper and lower surfaces: Smooth, glabrous; matte. Color: When opening and fully opened, upper surface: Close to a blend of 145A and 145B; with subsequent development, color becoming closer to 144C. Fully opened, lower surface: Close to 145C; with subsequent development, color becoming closer to 144C.

*Sepals, fertile flowers*.—Quantity and arrangement: Five in a single whorl. Length: About 1.5 mm. Width: About 1 mm. Shape: Broadly deltoid. Apex: Acute. Base: Broadly cuneate. Margin: Entire. Texture and luster, upper and lower surfaces: Smooth, glabrous; matte. Color: When opening and fully opened, upper surface: Close to 145B to 145C; color does not change with subsequent development. When opening and fully opened, lower surface: Close to 145C; color does not change with subsequent development.

*Pedicels, sterile flowers*.—Length: About 1.9 cm. Diameter: About 1 mm. Strength: Moderately strong. Aspect: About 0° to 45° from main peduncle axis. Texture and luster: Moderately pubescent; matte. Color: Close to 145D.

*Pedicels, fertile flowers*.—Length: About 1 mm. Diameter: About 0.5 mm. Strength: Moderately strong. Aspect: About 5° from peduncle axis. Texture and luster: Moderately pubescent; matte. Color: Close to 145D.

*Reproductive organs, sterile flowers*.—Stamens: Quantity per flower: Ten. Filament length: About 3 mm. Filament color: Close to NN155D. Anther shape: Oblong. Anther length: About 0.5 mm. Anther color: Close to 156D. Pollen amount: Scarce. Pollen color: Close to 161C. Pistils: Pistil quantity per flower: Three or four. Pistil length: About 1 mm. Stigma shape: Club-shaped. Stigma color: Close to 157C.

Style length: About 0.5 mm. Style color: Close to 157A. Ovary color: Close to 145C.

*Reproductive organs, fertile flowers*.—Stamens: Quantity per flower: Ten. Filament length: About 3 mm. Filament color: Close to NN155D. Anther shape: Oblong. Anther length: About 0.5 mm. Anther color: Close to 156D. Pollen amount: Scarce. Pollen color: Close to 161C. Pistils: Pistil quantity per flower: Three or four. Pistil length: About 1 mm. Stigma shape: Club-shaped. Stigma color: Close to 157C. Style length: About 0.5 mm. Style color: Close to 157A. Ovary color: Close to 145C.

*Fruits and seeds*.—To date, fruit and seed development has not been observed on plants of the new *Hydrangea*.

Pathogen & pest resistance: Plants of the new *Hydrangea* have not been observed to be resistant to pathogens and pests common to *Hydrangea* plants.

Temperature tolerance: Plants of the new *Hydrangea* have been shown to be suitable for USDA Hardiness Zones 5 through 9.

It is claimed:

1. A new and distinct *Hydrangea* plant named 'HYLV18539' as herein illustrated and described.

* * * * *